(12) United States Patent
Cully et al.

(10) Patent No.: US 9,603,693 B2
(45) Date of Patent: Mar. 28, 2017

(54) DUAL NET VASCULAR FILTRATION DEVICES AND RELATED SYSTEMS AND METHODS

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 757 days.

(21) Appl. No.: 13/961,503

(22) Filed: Aug. 7, 2013

(65) Prior Publication Data
US 2014/0046358 A1 Feb. 13, 2014

Related U.S. Application Data

(60) Provisional application No. 61/682,102, filed on Aug. 10, 2012.

(51) Int. Cl.
*A61F 2/01* (2006.01)
*A61F 2/86* (2013.01)
*A61F 2/91* (2013.01)
*A61F 2/82* (2013.01)

(52) U.S. Cl.
CPC .............. *A61F 2/01* (2013.01); *A61F 2/013* (2013.01); *A61F 2/86* (2013.01); *A61F 2/91* (2013.01); *A61F 2002/016* (2013.01); *A61F 2002/828* (2013.01)

(58) Field of Classification Search
CPC .... A61F 2/01; A61F 2/013; A61F 2/86; A61F 2/90; A61F 2/91; A61F 2002/011; A61F 2002/016; A61F 2002/828
See application file for complete search history.

(56) References Cited

U.S. PATENT DOCUMENTS

| | | | |
|---|---|---|---|
| 6,241,746 B1 | 6/2001 | Bosma et al. | |
| 6,635,070 B2 | 10/2003 | Leeflang et al. | |
| 6,712,835 B2 | 3/2004 | Mazzuchi et al. | |
| 6,719,775 B2 | 4/2004 | Slaker et al. | |
| 7,621,870 B2 | 11/2009 | Berrada et al. | |
| 8,313,503 B2 | 11/2012 | Cully et al. | |
| 2002/0173819 A1 | 11/2002 | Leeflang et al. | |
| 2003/0097145 A1 | 5/2003 | Goldberg et al. | |
| 2003/0176888 A1 | 9/2003 | O'Connell | |
| 2003/0181943 A1* | 9/2003 | Daniel | A61F 2/01 606/200 |

(Continued)

FOREIGN PATENT DOCUMENTS

WO 02/05888 1/2002

OTHER PUBLICATIONS

International Search Report for PCT/US2013/054303 mailed Sep. 26, 2013, corresponding to U.S. Appl. No. 13/961,503.

(Continued)

*Primary Examiner* — Todd J Scherbel

(57) ABSTRACT

According to one aspect of the disclosure, a dual net vascular filtration device comprises a central frame, a proximal filter net attached to a proximal end of the central frame, and a distal filter net attached to a distal end of the central frame. Upon deployment, the distal filter net can be configured to evert into the proximal filter net.

17 Claims, 9 Drawing Sheets

(56) References Cited

U.S. PATENT DOCUMENTS

2007/0233174 A1* 10/2007 Hocking ................ A61F 2/013
606/200
2009/0105747 A1   4/2009 Chanduszko et al.
2010/0168785 A1   7/2010 Parker
2012/0277787 A1  11/2012 Eggers

OTHER PUBLICATIONS

Wallace, MJ, Ogawa K, Wright K, Carrasco CH, Richli W, Charnsangavej C. Inferior Vena Caval Stent Filter. AJR 147: 1247-1250.

\* cited by examiner

DUAL NET VASCULAR FILTRATION DEVICES AND RELATED SYSTEMS AND METHODS

CROSS-REFERENCE TO RELATED APPLICATIONS

This application claims the priority benefit under 35 U.S.C. §119(e) of U.S. Provisional Application No. 61/682,102, filed Aug. 10, 2012, and the content of this patent application is incorporated herein in its entirety.

BACKGROUND

Field

The disclosure relates to vascular filtration of embolic debris.

Discussion of the Related Art

Circulation of embolic debris can cause mild to extreme cardiovascular complications, leading to pulmonary embolism and even death. Because prior art vascular filtration devices may not adequately confine embolic debris, dual net vascular filtration devices may be used. However, prior art dual net vascular filtration devices may have highly complicated geometries, leading to potential delivery and deployment obstacles. In addition, prior art vascular filtration devices may have geometries that facilitate unwanted tissue ingrowth due to having many contact points with the host vessel. There is thus ever a need for improved vascular filtration devices, systems and methods. The present disclosure addresses this need.

SUMMARY

Vascular filtration devices, systems and methods are provided. In accordance with some embodiments, a dual net vascular filtration device comprises a central frame, a proximal filter net attached to a proximal end of the central frame, and a distal filter net attached to a distal end of the central frame. Upon deployment, the distal filter net can be configured to evert into the proximal filter net. In some embodiments, the central frame has minimum contact points with the host vessel. In some embodiments, the central frame comprises a hinged portion. Related methods of making, systems, and methods of use are also disclosed herein.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

DETAILED DESCRIPTION OF THE ILLUSTRATED EMBODIMENTS

Figure 1A:
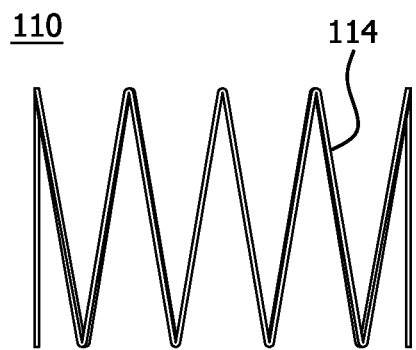
FIGS. 1A-1F illustrate central frames in accordance with embodiments of the present disclosure.

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms "downstream" or "antegrade" and "upstream" or "retrograde," when used herein in relation to the patient's vasculature, refer to the direction of blood flow and the direction opposite that of blood flow, respectively. In the venous system, "upstream" or "retrograde" refers to the direction moving away from the heart, while "downstream" or "antegrade" refers to the direction moving toward to the heart. In this regard, "antegrade vascular delivery" as used herein means delivered to a treatment site in the direction of blood flow.

Similarly, throughout this specification and in the claims, the term "proximal" refers to a location that is, or a portion of an endoluminal device (such as a stent-graft) that when implanted is, further downstream with respect to blood flow than another portion of the device. Similarly, the term "proximally" refers to the direction of blood flow or further downstream in the direction of blood flow.

The term "distal" refers to a location that is, or a portion of an endoluminal device that when implanted is, further upstream with respect to blood flow than another portion of the device. Similarly, the term "distally" refers to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

As used herein, an "elliptical" shape refers to any shape that generally lacks a point where two lines, curves, or surfaces converge to form an angle. For example, an "elliptical" shape encompasses traditional Euclidian geometric shapes such as circles and ellipses, as well as other non-angular shapes (that lack any angles), even if those shapes do not have designations common in Euclidian geometry.

As used herein, a "non-elliptical" shape refers to any shape that includes at least one point where two lines, curves, or surfaces converge to form an angle. For example, a "non-elliptical" shape encompasses traditional Euclidian geometric shapes such as triangles, rectangles, squares, hexagons, trapezoids, pentagons, stars, and the like as well as other shapes that have at least one angle even if those shapes do not have designations common in Euclidian geometry.

As used herein, "embolic debris" means biologic or non-biologic elements, the presence of which in the vasculature presents an embolic risk (including, but not limited to plaque, emboli, etc.).

As used herein, "anchor" refers to a tack, barb, hook, tine, surface modification, such as those described in U.S. Pub. No. 2012/0064273 to Bacino, which is hereby incorporated by reference in its entirety, or the like, which may be used to attach any portion of a vascular filtration device to a host vessel, or any portion of a vascular filtration device to another portion of the same.

As used herein, the term "elongate element" is generally any element configured for relative axial movement with an endoluminal device delivery element (e.g., a catheter-based endoluminal device delivery element such as a balloon catheter) and includes any longitudinally extending structure with or without a lumen therethrough. Thus, elongate elements include but are not limited to tubes with lumens (e.g., catheters), solid rods, hollow or solid wires (e.g., guidewires), hollow or solid stylets, metal tubes (e.g., hypotubes), polymer tubes, pull cords or tethers, fibers, filaments, electrical conductors, radiopaque elements, radioactive elements and radiographic elements. Elongate elements can be any material and can have any cross-sectional shape including, but not limited to, profiles that are elliptical, non-elliptical, or random.

In various embodiments, the present disclosure relates to a dual net vascular filtration device comprising a central frame, a proximal filter net, and a distal filter net.

The central frame can comprise a single or a plurality of adjacent frame elements. In accordance with various embodiments, adjacent frame elements can be connected apex to apex or with offset apices. Each individual frame element can in turn comprise a stent and/or a stent graft, the stent having a plurality of ring or helical stent elements, wherein each individual ring or helical stent element is linear or has a sinusoidal or zig-zag configuration or the like. Frame elements can comprise a shape-memory material, such as nitinol. In other embodiments, however, frame elements can be comprised of other materials, self-expandable or otherwise expandable (e.g., with a fluid-filled balloon), such as various metals (e.g., stainless steel), alloys and polymers to include bioabsorbable polymers.

Figure 1B:
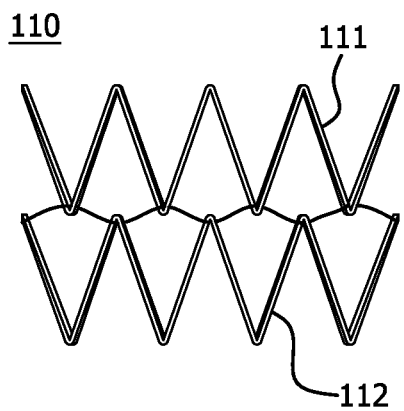
Figure 1C:
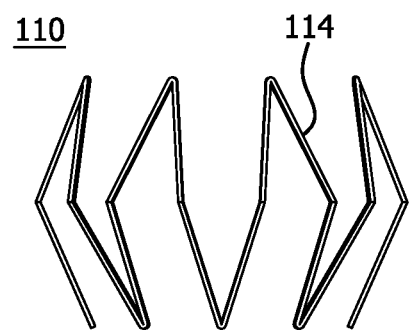
Figure 1D:
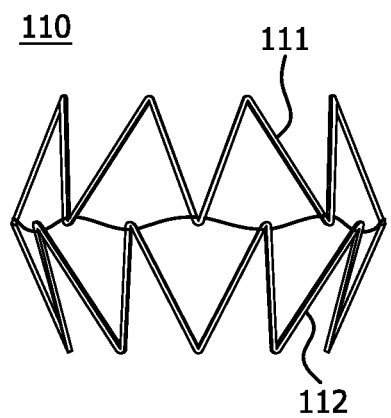
Figure 1E:
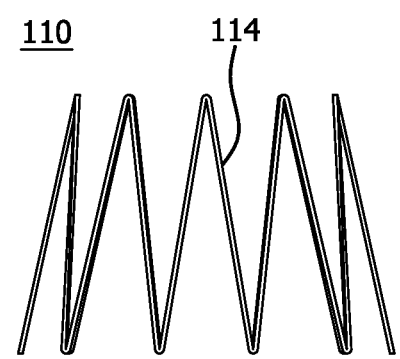

Turning now to the FIGS., a central frame 110 is illustrated in each of FIGS. 1A-1F. FIGS. 1A, 1C and 1E each illustrate central frame 110 having one frame element 114, while FIGS. 1B, 1D and 1F each illustrate central frame 110 having two adjacent frame elements 111 and 112. Of note, adjacent frame elements 111 and 112 need not have the same axial length. Indeed, shortening the axial length of a more distal frame element may assist in providing an open space subtended only by the filter nets once deployed.

With regard to FIG. 1C it is apparent that this embodiment may be made in an alternative fashion wherein the sharp bends of frame element 114 at the opposing ends of central frame 110 may be provided at the largest diameter of central frame 110. In such an embodiment the middle region of the length of central frame 110 would have a smaller diameter than at the two opposing ends of central frame 110.

The central frame can be configured to have circumferential contact with the host vessel, for example, by having a cross section that has an elliptical shape. For example, both of FIGS. 1A and 1B illustrates central frame 110 having a cross section that has an elliptical shape, more particularly, a circular or otherwise rounded cross section.

In other embodiments, further minimizing contact points with the host vessel may be desirable in embodiments when tissue ingrowth is unwanted above a particular threshold level, for example, to facilitate later removal from the host vessel. For instance, minimum contact points or minimum point loads may be appropriate for inferior vena cava applications. In this regard, the central frame can be configured to minimize contact points with the host vessel, for example, by having a cross section that is tapered, bulged, or cinched along its axial length and/or a cross section transverse to the axial length that has a non-elliptical shape. As such, central frame 110 can be constructed to contact the host vessel on only one or a plurality of discrete locations or points (e.g., at frame element apices or peripheries, or where adjacent frame elements are joined), rather than about the entire outer surface of central frame 110.

Figure 1F:
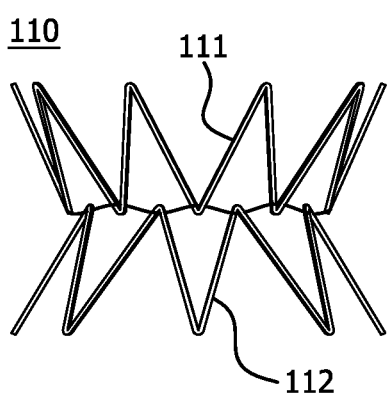

Both of FIGS. 1C and 1D illustrate central frame 110 having a cross section that is tapered along its axial length at both ends, while FIG. 1E illustrates central frame 110 having a cross section that is tapered along its axial length on only one end. Still further, FIG. 1F illustrates central frame 110 having a cross section that is tapered along its axial length toward the middle or an intermediate section, to form a waist. This particular embodiment may find applicability in minimizing or eliminating tipping of, or otherwise stabilizing, central frame 110.

Among other ways, the configurations described above may be made by using appropriately dimensioned mandrels (e.g., tapered), cinching a material used to loosely connect adjacent frame elements, bulging precursor designs, etc. Of note, the design illustrated in FIG. 1A may serve as a precursor to those illustrated in FIGS. 1C and 1E. Similarly, the design illustrated in FIG. 1B may serve as a precursor to those illustrated in FIGS. 1D and 1F.

In addition, the central frame can be configured to have a transverse cross section creating a shape that has an angled or undulating perimeter such as triangles, rectangles, squares, hexagons, trapezoids, pentagons, stars, and the like.

Figure 2A:
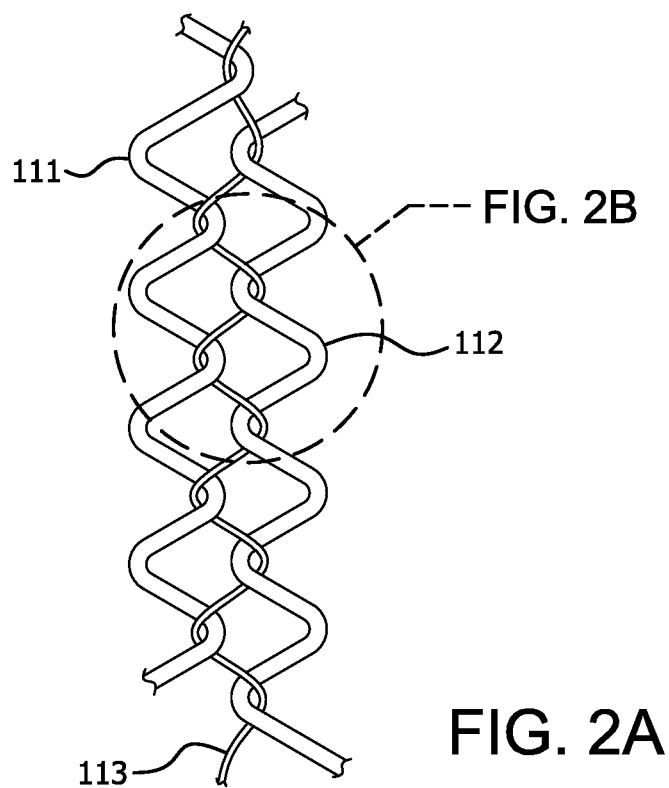
FIGS. 2A and 2B illustrate the connection of adjacent frame elements in accordance with embodiments of the present disclosure.
Figure 2B:
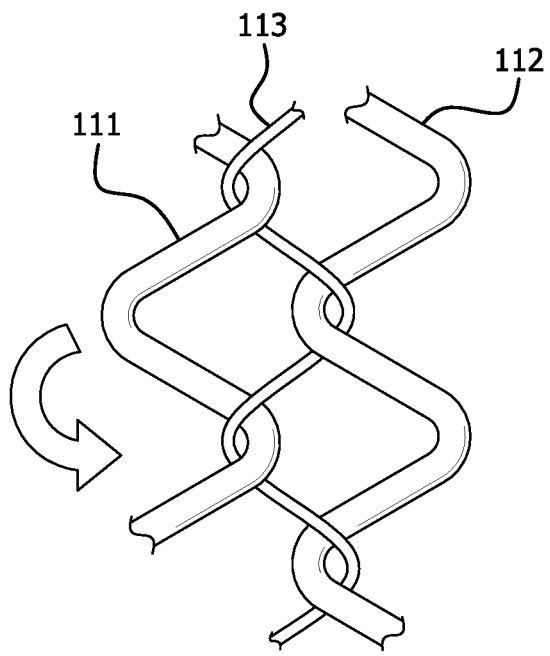
Figure 2C:
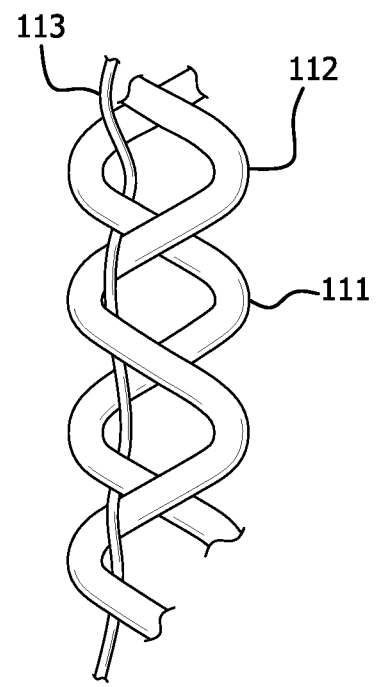
FIG. 2C illustrates the eversion of adjacent frame elements in accordance with embodiments of the present disclosure.

The central frame can further comprise a hinged portion, which can, but need not, coincide with minimum contact points with the host vessel. In general, the hinged portion can be configured to allow a distal portion of the central frame to evert with respect to a proximal portion of the central frame. (As used herein, the terms evert, everting, everted, eversion, as used herein refer to the act, condition, or ability of being turned inside out or vice versa. As used herein, a first frame element extends away from a second frame in a non-everted or un-everted condition, wherein the first frame element can be everted into the second frame element.) In this regard, the hinged portion can comprise loosely connected adjacent frame elements. For example, and with reference to FIGS. 2A and 2B, adjacent frame elements 111 and 112 can be loosely connected by lacing a polymeric material 113 through the apices of adjacent frame elements 111 and 112. FIG. 2B illustrates a close up view of a portion of what is illustrated in FIG. 2A, showing how element 111 will be rotated under element 112 during the everting process, resulting in the appearance shown in FIG. 2C.

Figure 3A:
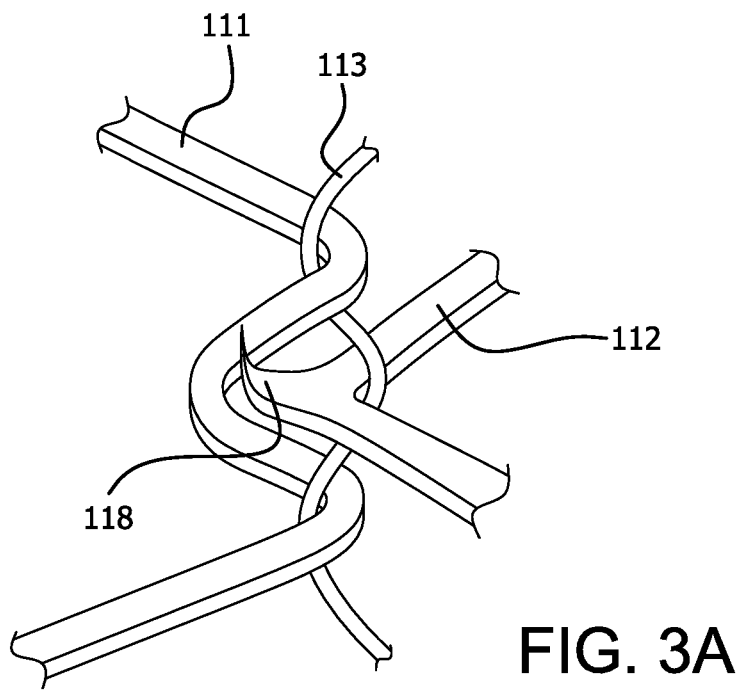
FIGS. 3A and 3B illustrate the connection of adjacent frame elements having anchors in accordance with embodiments of the present disclosure.
Figure 3B:
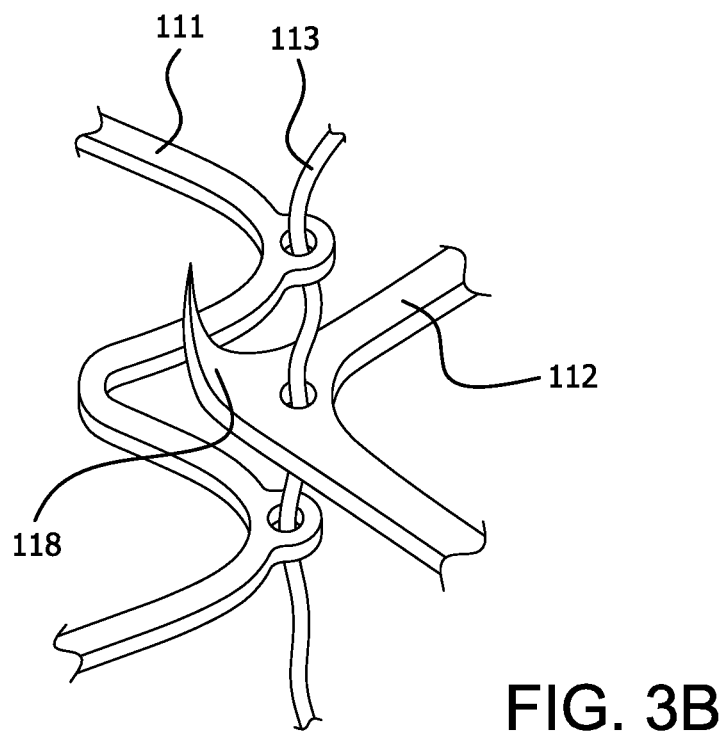

FIGS. 3A and 3B illustrate similar embodiments of loosely connecting adjacent frame elements 111 and 112. In FIG. 3A, adjacent frame elements 111 and 112 are connected by lacing polymeric material 113 through the apices of adjacent frame elements 111 and 112, while In FIG. 3B, adjacent frame elements 111 and 112 are connected by lacing polymeric material 113 through holes in the apices of adjacent frame elements 111 and 112.

Figure 4A:
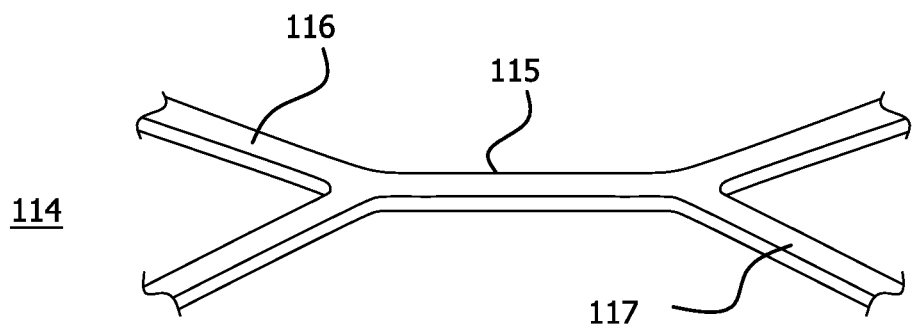
FIGS. 4A and 4B illustrate a frame element having a biased hinged portion in accordance with embodiments of the present disclosure.
Figure 4B:
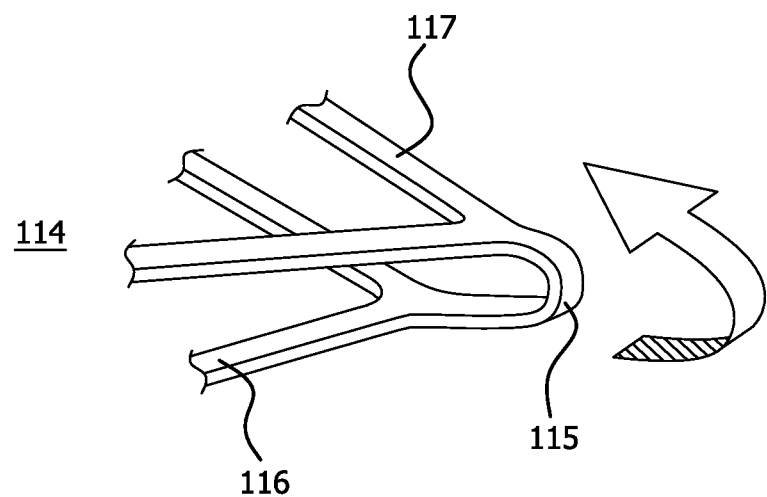

In other embodiments, the hinged portion can comprise adjacent frame elements connected by one or more flexible bridges, such as those described in U.S. Pub. No. 2012/0109283 to Burkart et al., which is hereby incorporated by reference in its entirety. In yet other embodiments, the hinged portion can comprise a single frame element having a weakened or biased portion. For example, and with reference to FIGS. 4A and 4B, single frame element 114 is illustrated as having a biased portion 115. FIG. 4B illustrates a distal portion 116 of single frame element 114 everted with respect to a proximal portion 117 of single frame element 114 at biased portion 115.

The central frame can comprise one or more anchors for attachment to the host vessel. In the alternative, or in addition, one or more independent anchors can be used to attach the central frame to the host vessel.

Anchors can, but need not, coincide with minimum contact points between the central frame and the host vessel. With momentary reference back to FIGS. 3A and 3B, illustrated in each is frame element 112 comprising an integral anchor 118. In such embodiments, anchor 118 may engage the host vessel upon eversion of one of adjacent frame elements 111 and 112 with respect to the other.

In various embodiments, and turning now to FIGS. 5A-5D, central frame 110 of a vascular filtration device 100 is attached to a proximal filter net 120 and a distal filter net 122. Such attachment may be movable (e.g., axially movable), releasable or permanent. By way of example, proximal filter net 120 can be attached to (or proximate to) a proximal end 117 of central frame 110, and distal filter net 122 can be attached to (or proximate to) a distal end 116 of central frame 110. In general, either or both of proximal filter net 120 and distal filter net 122 can be attached to (or proximate to) distal end 116, proximal end 117, or an intermediate portion of central frame 110. In this regard, proximal filter net 120 and distal filter net 122 can be attached to (or proximate to) portions of central frame 110 that have the same or different transverse cross sections.

Upon deployment, and with reference now to FIGS. 6A-6D, distal filter net 122 can be configured to evert into proximal filter net 120. Such eversion may occur at distal end 116 of central frame 110 (see FIGS. 6A, 6B and 6D), proximal end 117 of central frame 110, or therebetween such as at a hinged portion of central frame 110 (see FIG. 6C). Such eversion may also occur at a crease, fold, inflection, or the like of a filter net. Eversion of distal filter net 122 net into proximal filter net 120 can be accomplished by relative axial movement of elongate elements (as discussed infra), and/or by the flow of blood through distal filter net 122 (as illustrated in FIG. 7B).

Figure 5A:
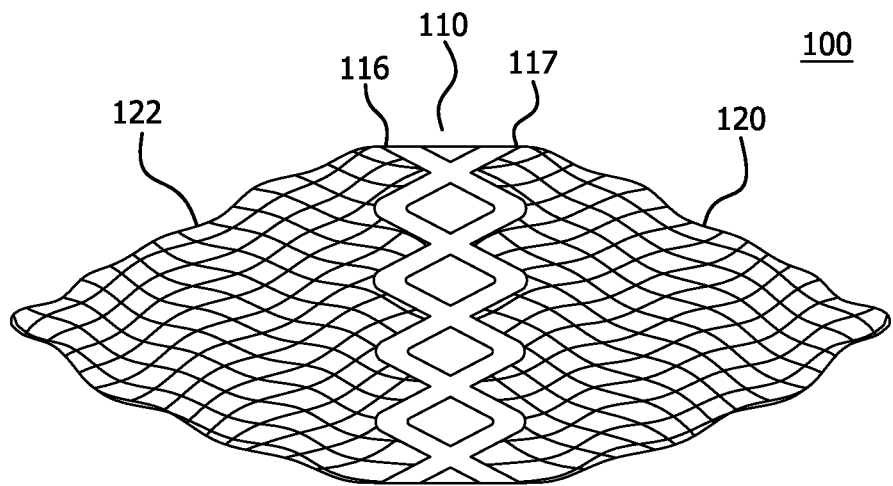
FIGS. 5A-5D illustrate vascular filtration devices in accordance with embodiments of the present disclosure.
Figure 5B:
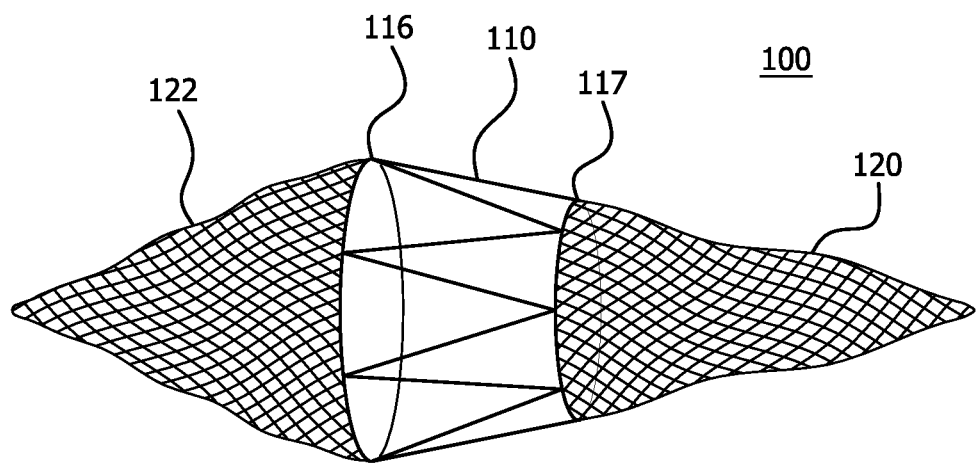
Figure 5C:
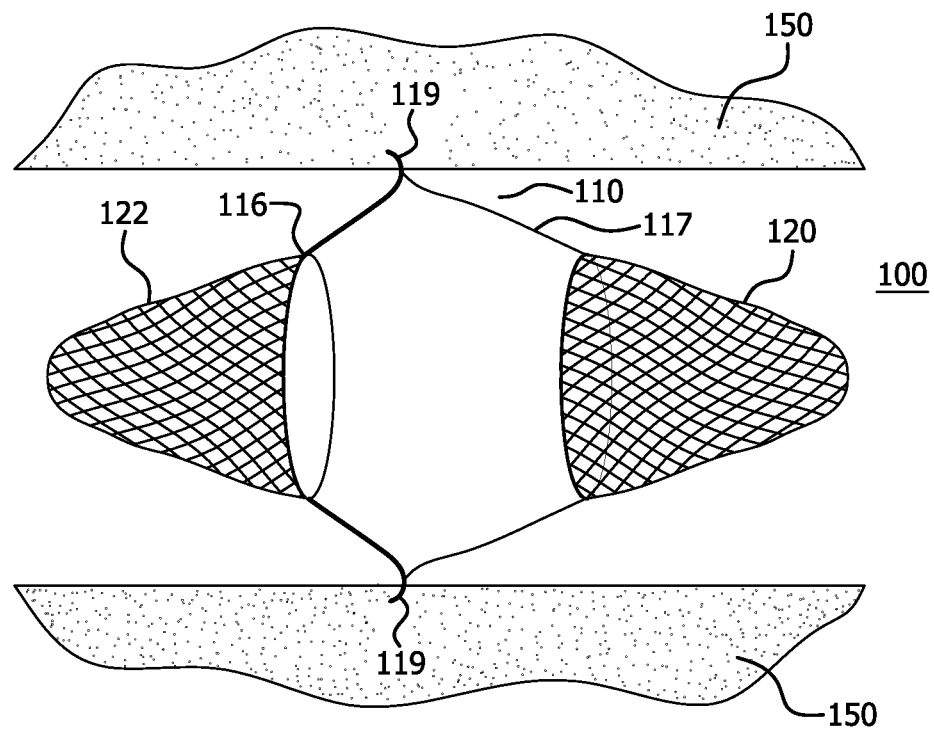
Figure 5D:
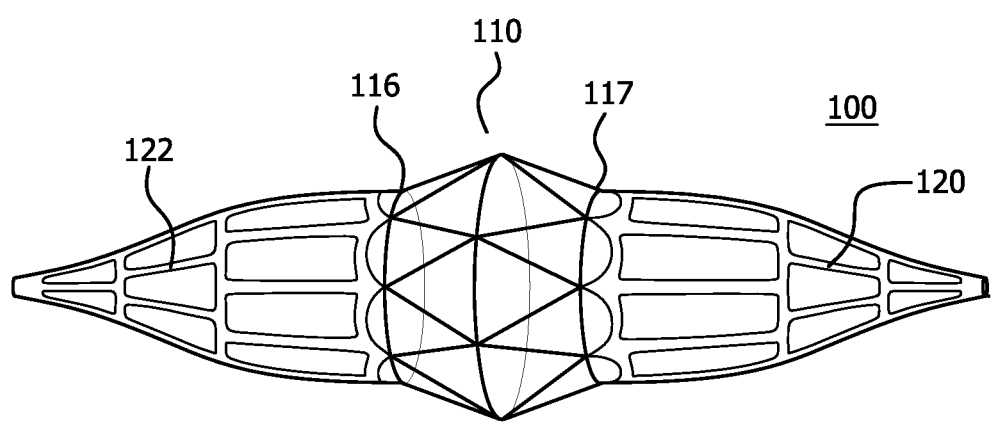
Figure 6A:
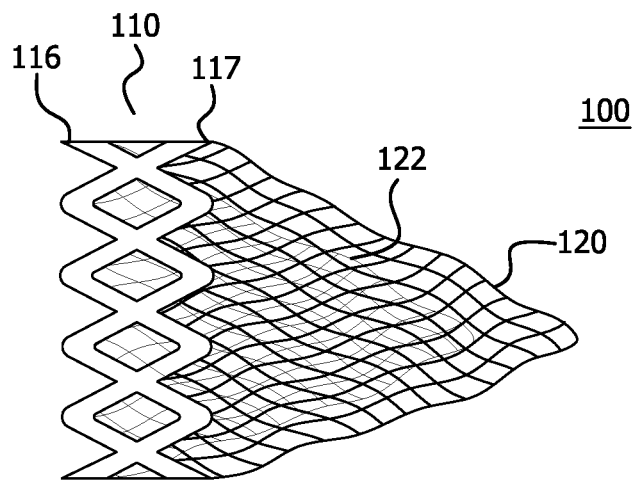
FIGS. 6A-6D illustrate everted vascular filtration devices in accordance with embodiments of the present disclosure.
Figure 6B:
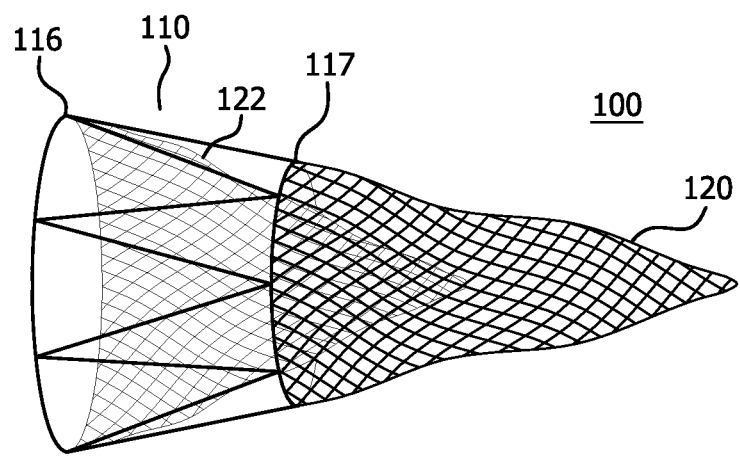
Figure 6C:
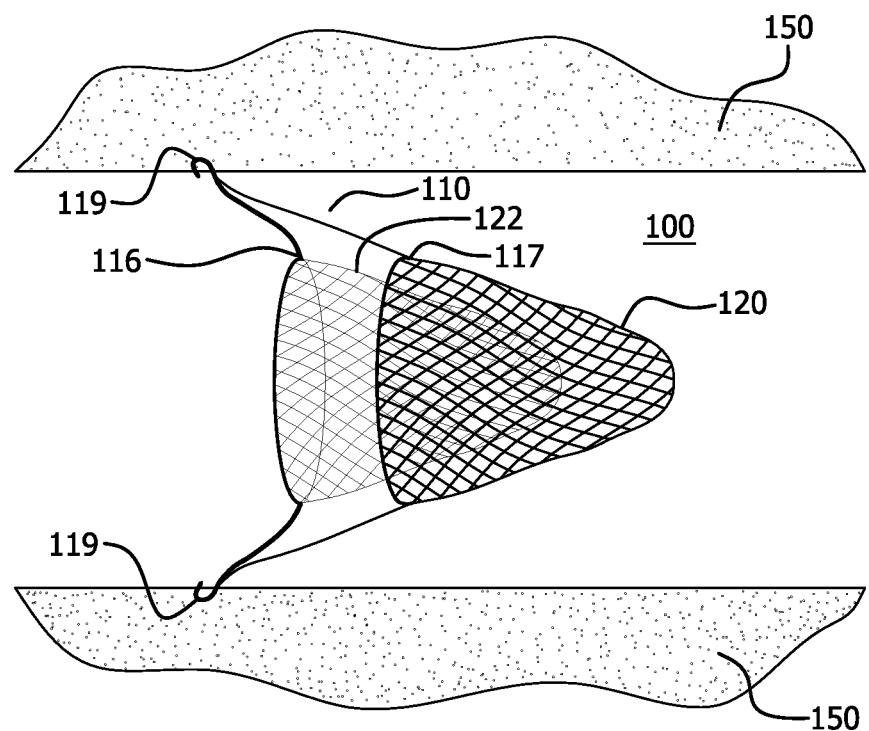
Figure 6D:
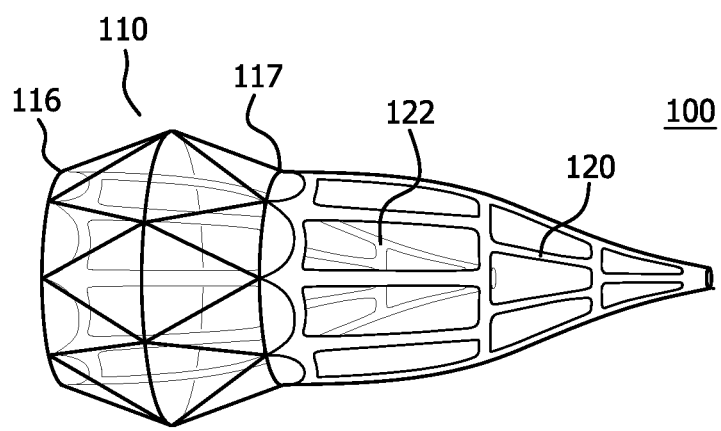

In various embodiments, and with particular reference to FIGS. 5C and 6C, central frame 110 can comprise one or more anchors 119. Upon eversion of distal filter net 122 into proximal filter net 120, anchors 119 can grasp into a host vessel 150.

The proximal and distal filter nets can comprise one or more filter elements, for example, sutures, threads, fibers, tubular elements, braids, meshes, lattices, wires, or ring or helical stent elements, any the foregoing, whether laser cut from a tube, formed separately, or otherwise.

Filter elements can comprise various materials including, but not limited to polymers, such as fluoropolymers like an expanded polytetrafluoroethylene ("ePTFE"), expanded PTFE, expanded modified PTFE, expanded copolymers of PTFE, nylons, polycarbonates, polyethylenes, polypropylenes and the like. Filter elements can also comprise various elastomeric materials.

A filter element can comprise a tubular element or microporous material, wherein the tubular element or microporous material are impermeable. This can be accomplished by the tubular element itself comprising an impermeable polymer such as polyurethane, and having a lumen which is sealed or isolated from the external environment. Alternatively, a microporous material or the tubular element can have an impermeable coating, such as that described in U.S. Pat. No. 7,049,380 to Chang et al., which is hereby incorporated by reference in its entirety, which in effect seals or isolates the porous microstructure or the lumen of the tubular element from the external environment. In such embodiments, the tubular element or microporous material may serve as a "reservoir" for air, foam, or any other medium, thus resulting in a desired radio-opacity, echogenicity, buoyancy, etc. Such embodiments may find particular applicability when the host vessel comprises a portion of the inferior vena cava.

In addition, filter elements can comprise a shape-memory material, such as nitinol. In other embodiments, however, filter elements can be comprised of other materials, self-expandable or otherwise expandable (e.g., with a fluid-filled balloon), such as various metals (e.g., stainless steel), alloys and polymers.

The proximal and distal filter nets can comprise the same or different material. Similarly, the proximal and distal filter nets can comprise the same or different opening size(s). In various embodiments, at least one of the proximal and distal filter nets is configured to confine embolic debris (i.e., not be permeable to embolic debris) greater than or equal to about 10 mm, about 1 mm, and/or about 100 µm (as measured lengthwise across its longest dimension). Such confinement may result from the respective filter net(s) having an average opening size less than or equal to about 10 mm, about 1 mm, and/or about 100 µm (as measured lengthwise across its longest dimension). Confinement of embolic debris, and thus the average opening size, may vary along or about a filter net.

The proximal and distal filter nets can also comprise the same or different dimensions. In various embodiments, the dimensions are substantially the same such that a vascular filtration device may be bidirectional, as the device can be deployed in an antegrade or retrograde direction, and similarly, can be retrieved in either direction. In other words, either filter net can be everted into the other.

In other embodiments, the dimensions are not substantially the same or respective attachment points are configured such that the distal filter net can be configured to evert into the proximal filter net and provides an open space subtended only by the filter nets once deployed. In other words, one filter net can be shorter or more shallow than the other. For example, and with reference to FIGS. 5C, 6C, 7A, and 7B, distal filter net 122 can be shorter than proximal filter net 120.

In an embodiment, the apertures within the filter nets can be off set from each other or staggered, which in effect, creates a more dense or smaller aperture mesh or lattice network. In addition, the dimensions of the filter nets and/or their respective central frame attachment site can be configured such that, upon deployment, the everted filter net is in contact with the other filter net, which can further create a more dense or smaller aperture mesh or lattice network.

Any portion of a dual net vascular filtration device can comprise elements which are passed through and/or attached at or near its proximal and/or distal end to facilitate or otherwise assist in the delivery and/or retrieval of the vascular filtration device. Such elements may include one or more radio-opaque or echogenic elements, and/or surface elements or other mechanisms that facilitate coupling with the elongate element discussed infra, for example, hooks, barbs, snares, loops, tethers, detents, or the like.

Any portion of a dual net vascular filtration device can comprise a therapeutic agent, for example, be coated or imbibed with a therapeutic agent, whether dry, gel or liquid. Examples of therapeutic agents comprise antiproliferative/ antimitotic agents including natural products such as vinca alkaloids (i.e. vinblastine, vincristine, and vinorelbine), paclitaxel, epidipodophyllotoxins (i.e. etoposide, tenipo-side), antibiotics (dactinomycin (actinomycin D) daunoru-bicin, doxorubicin and idarubicin), anthracyclines, mitoxan-trone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)IIbIIIa inhibitors and vit-ronectin receptor antagonists; antiproliferative/antimitotic alkylating agents such as nitrogen mustards (mechlore-thamine, cyclophosphamide and analogs, melphalan, chlorambucil), ethylenimines and methylmelamines (hex-amethylmelamine and thiotepa), alkyl sulfonates-busulfan, nitrosoureas (carmustine (BCNU) and analogs, streptozo-cin), trazenes-dacarbazinine (DTIC); antiproliferative/an-timitotic antimetabolites such as folic acid analogs (metho-trexate), pyrimidine analogs (fluorouracil, floxuridine, and cytarabine), purine analogs and related inhibitors (mercap-topurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and uroki-nase), aspirin, dipyridamole, ticlopidine, clopidogrel, abcix-imab; antimigratory; antisecretory (breveldin); anti-inflam-matory: such as adrenocortical steroids (cortisol, cortisone, fludrocortisone, prednisone, prednisolone, 6α-methylpred-nisolone, triamcinolone, betamethasone, and dexametha-sone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (aura-nofin, aurothioglucose, gold sodium thiomalate); immuno-suppressives: (cyclosporine, tacrolimus (FK-506), sirolimus (rapamycin), azathioprine, mycophenolate mofetil); angio-genic agents: vascular endothelial growth factor (VEGF), fibroblast growth factor (FGF) platelet derived growth factor (PDGF), erythropoetin; angiotensin receptor blocker; nitric oxide donors; anti-sense oligionucleotides and combinations thereof; cell cycle inhibitors, mTOR inhibitors, growth factor signal transduction kinase inhibitors, chemical compound, biological molecule, nucleic acids such as DNA and RNA, amino acids, peptide, protein or combinations thereof.

Any portion of a dual net vascular filtration device can comprise a radio-opaque or echogenic element (e.g., markers or bands) that enhances imaging or detection during and/or following delivery or deployment. Such elements can be comprised of one or more of tungsten, gold, platinum and the like.

The present disclosure further relates to methods of making a vascular filtration device. In various embodiments, filter nets in accordance with the present disclosure are made by winding one or more polymeric sutures about a tapered mandrel (e.g., a jig) in crossing helical patterns so as to form mesh or lattice networks having the desired opening size(s). In some embodiments, the helical pattern crossing points are powder coated with fluorinated ethylene propylene ("FEP") and the construct is heated at 320 degrees Celsius for 4-5 minutes. In other embodiments, one or more sacrificial polyimide films (e.g., Kapton® by DuPont™) are placed on the mandrel (i.e., under the construct) and over the construct including the helical pattern crossing points, the construct is heated at 370 degrees Celsius for 4-5 minutes, and sintered. Filter nets are in turn attached to the central frame in accordance with any of the several embodiments described supra. In yet other embodiments, methods of making such structures, such as those described in U.S. Pat. No. 7,736,739 to Lutz et al., which is hereby incorporated by reference in its entirety, may be used.

In various embodiments, filter nets in accordance with the present disclosure are made by laser cutting openings in one or more polymeric sheets so as to form mesh or lattice networks having the desired opening size(s). Filter nets are in turn attached to the central frame as described supra.

In yet other embodiments, filter nets comprise one or more polymeric webs, which in turn attach filter nets to the central frame, for example, according to the methods described in U.S. Pub. No. 2012/0109283 to Burkart et al., which is hereby incorporated by reference in its entirety.

The present disclosure further relates to systems comprising a vascular filtration device. In various embodiments, a vascular filtration device and/or a portion thereof is attached to an elongate element. Such attachment may be movable (e.g., axially movable), releasable or permanent. In various embodiments, an elongate element can be configured to remain within the host vessel together with the vascular filtration device for an extended period of time, for example, hours, days, weeks or more. In other embodiments, an elongate element can be configured to be retrieved shortly after delivery of the vascular filtration device to the host vessel.

In various embodiments, an elongate element passes through the interior of a vascular filtration device, for example, through openings in the distal and proximal ends of the distal and proximal filter nets respectively. In other embodiments, an elongate element is attached to the exterior of a vascular filtration device. An elongate element can be configured to facilitate tension being applied across the vascular filtration device, so as to un-evert and/or collapse a central frame, in order to retrieve or relocate the device.

An elongate element can be further configured to provide a working lumen through which embolic debris can be aspirated and/or through which a therapeutic agent, as that term has been described above, can be delivered to a host vessel.

In addition, an elongate element can comprise further elements which are passed through and/or attached at or near the proximal and/or distal end of the elongate element to facilitate or otherwise assist in the delivery and/or retrieval of the vascular filtration device. Such elements may include one or more radio-opaque or echogenic elements, and/or surface elements or other mechanisms that facilitate coupling with the vascular filtration device, for example, hooks, barbs, snares, loops, tethers, detents, or the like.

In various embodiments, a vascular filtration device and/or a portion thereof is restrained or otherwise covered in a radially collapsed delivery configuration by a releasable or removable cover such as a sleeve, sheath, sock or other constraining mechanism. In other embodiments, a vascular filtration device and/or a portion thereof is restrained or otherwise covered in a radially collapsed delivery configuration by a surrounding elongate element until it is deployed therefrom by relative axial movement of a vascular filtration device and the surrounding elongate element. Deployment of a vascular filtration device can occur proximal to distal, distal to proximal, ends inward, center outward, etc. In various embodiments, retrieval of a vascular filtration device can be accomplished by withdrawal into a surrounding elongate element, such as an elongate member having a flared or conical distal end that can encompass and optionally, envelop the filtration device. In the alternative, or in addition, retrieval of a vascular filtration device can be enabled by incorporating into the delivery system one or more radio-opaque or echogenic elements, and/or surface elements or other mechanisms, for example, hooks, barbs, snares, loops, tethers, detents, or the like.

Figure 7A:
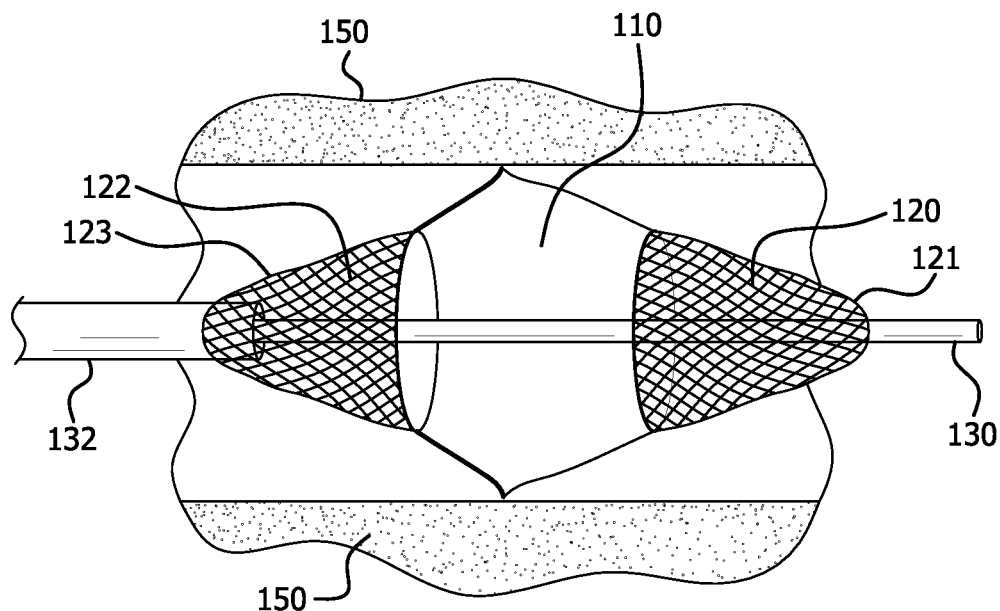
FIGS. 7A and 7B illustrate a vascular filtration system in accordance with embodiments of the present disclosure.
Figure 7B:
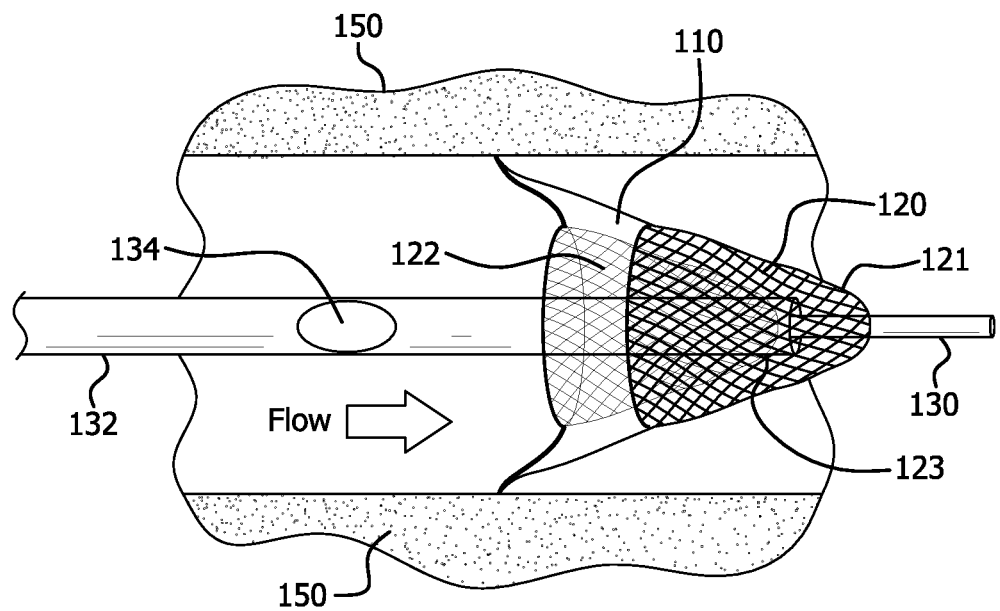

In various embodiments, and with reference finally to FIGS. 7A and 7B, a proximal end 121 of proximal filter net 120 is attached to an inner elongate element 130, while a distal end 123 of distal filter net 122 is attached to an outer elongate element 132. As illustrated in FIG. 7B, eversion of distal filter net 122 into proximal filter net 120 at central frame 110 can be accomplished by relative axial movement of elongate elements 130 and 132, while in a host vessel 150. As noted above, in various embodiments, at least one of inner elongate element 130 and outer elongate element 132 can be configured to remain within the host vessel together with the vascular filtration device for an extended period of time, for example, hours, days, weeks or more. In this regard, anchors may not be necessary to attach any portion of a vascular filtration device to host vessel 150.

In some embodiments, elongate element 132 can comprise an aperture 134. If proximal filter net 120 and/or distal filter net 122 were to become full (plugged) with embolic debris, aperture 134, communicating with the lumen of elongate element 132, could act as a temporary shunt to get blood past the blockage.

The present disclosure further relates to methods of use for a vascular filtration device. One such method comprises antegrade vascular delivery of a vascular filtration device to a host vessel in a radially collapsed delivery configuration, deploying the vascular filtration device from either a releasable or removable cover or a surrounding elongate element, everting one filter net with respect to another as described supra, filtering embolic debris, and retrieving the vascular filtration device.

It will be apparent to those skilled in the art that various modifications and variations can be made in the present disclosure without departing from the spirit or scope of the disclosure. For example, while embodiments of the present disclosure have been described with reference to the inferior vena cava, embodiments are scaleable and applications in various central and peripheral vessels and lumens are contemplated herein. Additionally, while embodiments of the present disclosure have been described with reference to two filter nets, one or any number of filter nets are contemplated herein. Further still, the embodiments can be used in connection with not just humans, but also various organisms having mammalian anatomies. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

We claim:

1. A vascular filtration device comprising a central frame, a proximal filter net attached proximate to a proximal end of the central frame, and
   a distal filter net attached proximate to a distal end of the central frame,
   wherein the distal filter net is configured to evert into the proximal filter net upon deployment in a host vessel;
   wherein the central frame comprises a hinged portion formed by a first frame element and a second frame element adjacent to the first frame element, the first frame element being connected to the second frame element such that the first frame element is rotatable under the second frame element to allow the distal end of the central frame to evert with respect to the proximal end of the central frame.

2. A vascular filtration device as in claim 1, wherein the central frame comprises a cross section that is tapered along its axial length.

3. A vascular filtration device as in claim 1, wherein the central frame comprises a cross section that has a non-elliptical shape.

4. A vascular filtration device as in claim 1, wherein the hinged portion comprises loosely connected adjacent frame elements.

5. A vascular filtration device as in claim 1, wherein the hinged portion comprises adjacent frame elements connected by one or more flexible bridges.

6. A vascular filtration device as in claim 1, wherein at least one of the proximal filter net and the distal filter net comprises a heparin coating.

7. A vascular filtration device as in claim 1, wherein the proximal filter net can further be configured to evert into the distal filter net upon deployment in the host vessel such that the device can be deployed or retrieved in either an antegrade or retrograde direction.

8. A vascular filtration device as in claim 7, wherein the distal filter net is dimensionally smaller than the proximal filter net so as to provide an open space subtended only by the proximal filter net and the distal filter net upon eversion of the distal filter net into the proximal filter net.

9. A system for confinement of embolic debris comprising:
   a vascular filtration device attached to an elongate element;
   wherein the vascular filtration device comprises a central frame, a proximal filter net attached proximate to a proximal end of the central frame, and a distal filter net attached proximate to a distal end of the central frame wherein the central frame comprises a hinged portion formed by separate, adjacent frame elements that are loosely connected end-to-end such that one of the adjacent frame elements is rotatable under the other of the adjacent frame elements to allow the distal end of the central frame to evert with respect to the proximal end of the central frame; and wherein the distal filter net is configured to evert into the proximal filter net upon deployment in a host vessel.

10. A system for confinement of embolic debris as in claim 9, wherein the elongate element is an inner catheter.

11. A system for confinement of embolic debris as in claim 9, wherein the vascular filtration device is restrained or otherwise covered in a radially collapsed delivery configuration by a releasable or removable cover.

12. A system for confinement of embolic debris as in claim 9, wherein the vascular filtration device is restrained or otherwise covered in a radially collapsed delivery configuration by a surrounding elongate element.

13. A system for confinement of embolic debris as in claim 12, wherein the surrounding elongate element is an outer catheter.

14. A system for confinement of embolic debris as in claim 9, wherein the proximal filter net can further be configured to evert into the distal filter net upon deployment in the host vessel such that the device can be deployed or retrieved in either an antegrade or retrograde direction.

15. A method for confinement of embolic debris comprising:

delivering a vascular filtration device to a host vessel in a radially collapsed delivery configuration, wherein the vascular filtration device comprises a central frame, a proximal filter net attached proximate to a proximal end of the central frame, and a distal filter net attached proximate to a distal end of the central frame wherein the central frame is configured to have minimum contact points with the host vessel and comprises a hinged portion formed by separate adjacent frame elements connected to one another, one of the adjacent frame elements being rotatable under the other of the adjacent frame elements to allow the distal end of the central frame to evert with respect to the proximal end of the central frame;

deploying the vascular filtration device from either a releasable or removable cover or a surrounding elongate element:

everting the distal filter net into the proximal filter net;

filtering embolic debris; and retrieving the vascular filtration device from the host vessel.

16. A method for confinement of embolic debris as in claim 15, wherein at least one of the proximal filter net and the distal filter net comprises a heparin coating.

17. A method for confinement of embolic debris as in claim 15, wherein the distal filter net is dimensionally smaller than the proximal filter net so as to provide an open space subtended only by the proximal filter net and the distal filter net upon eversion of the distal filter net into the proximal filter net.

* * * * *